United States Patent
Or et al.

(10) Patent No.: US 10,980,553 B2
(45) Date of Patent: Apr. 20, 2021

(54) REMODELING OF CALCIFIED AORTIC VALVE LEAFLETS

(71) Applicant: Pi-Cardia Ltd., Rehovot (IL)

(72) Inventors: Darr Or, Tel Nof (IL); Ofir Gal-Or, Gedera (IL); Ronnie Levy, Kochav-Yair (IL); Erez Golan, Rehovot (IL)

(73) Assignee: Pi-Cardia Lid., Rehovot (IL)

( * ) Notice: Subject to any disclaimer, the term of this patent is extended or adjusted under 35 U.S.C. 154(b) by 238 days.

(21) Appl. No.: 16/087,649

(22) PCT Filed: Mar. 29, 2017

(86) PCT No.: PCT/IB2017/051798
§ 371 (c)(1),
(2) Date: Sep. 23, 2018

(87) PCT Pub. No.: WO2017/168345
PCT Pub. Date: Oct. 5, 2017

(65) Prior Publication Data
US 2020/0323545 A1 Oct. 15, 2020

Related U.S. Application Data

(60) Provisional application No. 62/315,810, filed on Mar. 31, 2016.

(51) Int. Cl.
*A61B 17/22* (2006.01)
*A61B 90/00* (2016.01)
(Continued)

(52) U.S. Cl.
CPC ............ *A61B 17/22* (2013.01); *A61B 17/221* (2013.01); *A61B 17/320725* (2013.01);
(Continued)

(58) Field of Classification Search
CPC . A61B 17/22; A61B 17/221; A61B 17/22012; A61B 17/22031; A61B 17/22022
See application file for complete search history.

(56) References Cited

U.S. PATENT DOCUMENTS

2009/0306582 A1 12/2009 Granada
2010/0228277 A1* 9/2010 Pedersen ................ A61F 2/013
606/194

(Continued)

OTHER PUBLICATIONS

PCT Search Report and Written Opinion PCT/IB2017/081798, dated Jun. 21, 2017.

*Primary Examiner* — Vi X Nguyen
(74) *Attorney, Agent, or Firm* — Dekel Patent Ltd.; David Klein

(57) ABSTRACT

A calcification treatment device includes an outer body (12) including an inner cavity and at least one outer calcification treatment member (16) facing towards the inner cavity. An inner body (18) is movable into the inner cavity and includes at least one inner calcification treatment member (20) facing towards an inner surface of the outer body. One of the outer and inner calcification treatment members includes an expandable treatment member and one of the outer and inner calcification treatment members includes one or more fracturing elements capable of fracturing a calcification of a valve tissue.

13 Claims, 5 Drawing Sheets

(51) Int. Cl.
*A61B 17/221* (2006.01)
*A61B 17/3207* (2006.01)
(52) U.S. Cl.
CPC .... *A61B 90/03* (2016.02); *A61B 2017/22051* (2013.01); *A61B 2017/22098* (2013.01)

(56) References Cited

U.S. PATENT DOCUMENTS

| | | |
|---|---|---|
| 2011/0118634 A1 | 5/2011 | Golan |
| 2012/0253358 A1* | 10/2012 | Golan .............. A61B 17/22031 606/128 |
| 2013/0018396 A1 | 1/2013 | Gunderson |
| 2014/0316428 A1 | 10/2014 | Golan |

* cited by examiner

REMODELING OF CALCIFIED AORTIC VALVE LEAFLETS

FIELD OF THE INVENTION

The present invention generally relates to the repair of aortic and other cardiac valves, and more particularly to devices and methods for remodeling of calcified aortic valve leaflets.

BACKGROUND OF THE INVENTION

PCT Patent Applications PCT/US2010/058810 and PCT/US2012/067812, assigned to the present assignee, describe devices for fracturing calcifications in heart valves. The device includes a catheter that has an expandable stabilizer, an impactor shaft and an internal shaft, all disposed in an external shaft. Expandable impactor arms are mounted on the impactor shaft. The internal shaft is movable to cause the impactor arms to expand outwards and be locked in an expanded shape. An impacting element is movable to cause the impactor arms, while in the expanded shape, to move towards the tissue with sufficient energy so as to fracture a calcification located in tissue which is fixed by the stabilizer in a certain position vis-à-vis the impactor arms. The internal shaft may be lockable relative to the impactor shaft so that the impactor arms are fixed.

The impaction struts and stabilizer are shaped in accordance with a shape of the desired fracture site, e.g., leaflet bases (close to the annulus) and central folding lines of the native valve. Accordingly, the shapes of the impaction struts and of the stabilizer may include portions with a bicuspid shape, a tricuspid shape, or a semilunar shape, and may additionally have a portion with a depression corresponding to the folding lines, depending on the valve to be treated. Due to these predetermined shapes, the impactor, by impacting against the stabilizer, is able to generate fractures along the leaflet bases (close to the annulus) and central folding lines of the valve.

SUMMARY OF THE INVENTION

The present invention seeks to provide devices and methods for the repair of aortic and other cardiac valves, and in particular, remodeling (i.e., changing the structure and/or mobility) of calcified aortic valve leaflets.

The term "fracture" refers to any kind of reduction in size or any modification in shape or form, such as but not limited to, fracturing, pulverizing, cutting, breaking, grinding, chopping and the like.

It is noted that the invention is not only useful for treating heart valves, but also has application in cardio-vascular tissue in general.

There is provided in accordance with an embodiment of the invention a calcification treatment device including an outer body including an inner cavity and at least one outer calcification treatment member facing towards the inner cavity, an inner body movable into the inner cavity and including at least one inner calcification treatment member facing towards an inner surface of the outer body, wherein one of the outer and inner calcification treatment members includes an expandable treatment member and one of the outer and inner calcification treatment members includes one or more fracturing elements capable of fracturing a calcification of a valve tissue.

In accordance with an embodiment of the present invention the expandable treatment member is arranged for buckling radially outwards.

In accordance with an embodiment of the present invention the expandable treatment member includes an expandable mesh.

In accordance with an embodiment of the present invention the expandable treatment member includes an expandable balloon.

In accordance with an embodiment of the present invention the at least one inner calcification treatment member includes the expandable treatment member and the at least one outer calcification treatment member includes the one or more fracturing elements.

In accordance with an embodiment of the present invention the expandable treatment member and the one or more fracturing elements are concentric with each other. Alternatively, they are not concentric with each other.

In accordance with an embodiment of the present invention in a contracted orientation the expandable treatment member is passable through cusps of a valve.

There is provided in accordance with an embodiment of the present invention a method for fracturing calcifications in a heart valve including introducing the device to a valve, positioning a valve tissue, which has a calcification, between the one or more fracturing elements and the expandable treatment member, and expanding the expandable treatment member against the tissue to force the calcification against the one or more fracturing elements so as to fracture the calcification.

BRIEF DESCRIPTION OF THE DRAWINGS

The present invention will be understood and appreciated more fully from the following detailed description, taken in conjunction with the drawings in which.

DETAILED DESCRIPTION OF EMBODIMENTS

Figure 1:
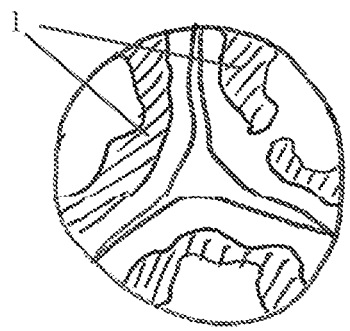
FIG. 1 is a simplified pictorial illustration of a calcified aortic valve of the prior art.

FIG. 1 illustrates a calcified aortic valve, with the calcifications being designated by numeral 1.

Figure 2:
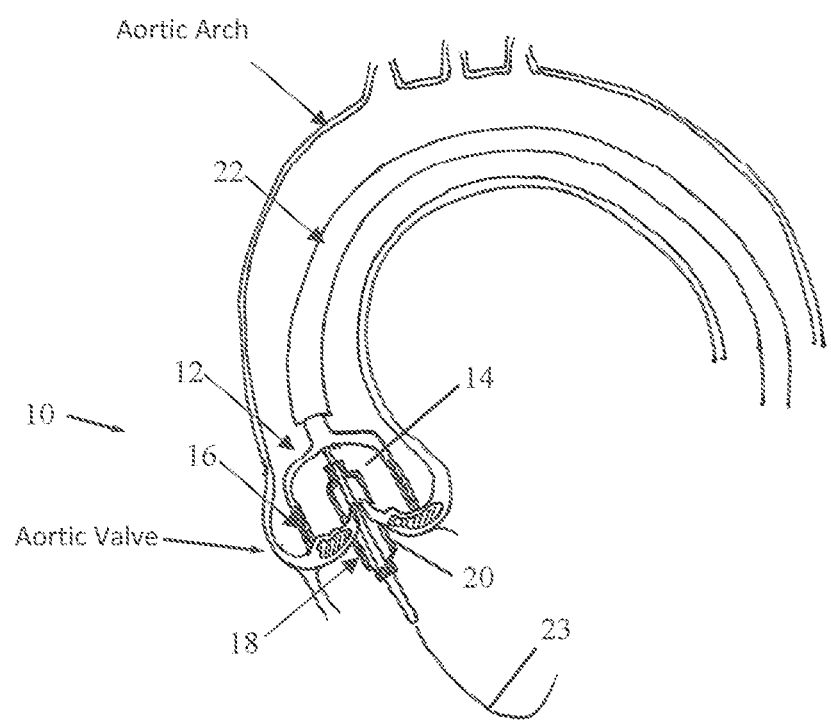
FIG. 2 is a simplified pictorial illustration of a calcification treatment device, constructed and operative in accordance with a non-limiting embodiment of the present invention, in which a distal end of a catheter of the calcification treatment device is shown placed on an aortic valve.

Reference is now made to FIG. 2, which illustrates a calcification treatment device 10, in accordance with a non-limiting embodiment of the invention.

Figure 3:
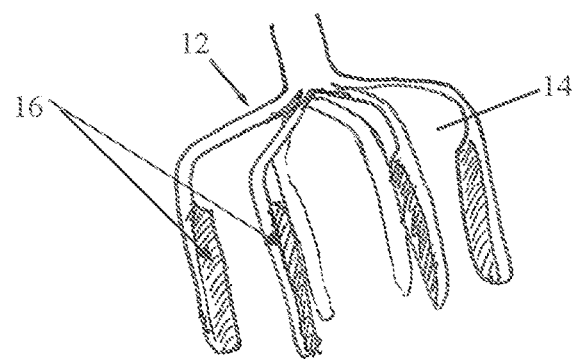
FIG. 3 is a simplified pictorial illustration of fracturing elements of the calcification treatment device, in accordance with a non-limiting embodiment of the present invention.

The calcification treatment device 10 includes an outer body 12 including an inner cavity 14. The outer body 12 includes one or more outer calcification treatment members 16 facing towards the inner cavity 14. The outer calcification treatment members 16 may be discrete members separated from each other by gaps, or may be one continuous member that may span part of or all the periphery of the outer body 12. In the illustrated embodiment, shown in FIG. 3, outer calcification treatment members 16 are individual fracturing elements 16 spaced from one another. The spacing may be uniform or varying. The shape and/or size of the fracturing elements 16 may be identical or one or more of them may be shaped and/or sized differently than others. Examples of fracturing elements 16 include, without limitation, knife-edge blades, roughened surfaces, grinding surfaces, cutting surfaces and others. The outer calcification treatment members 16 may be made as one integral part with the outer body 12 or may be made separately and connected thereto, such as by welding or any other method.

Referring again to FIG. 2, the calcification treatment device 10 includes an inner body 18 movable into the inner cavity 14. The inner body 18 includes one or more inner calcification treatment members 20 facing towards an inner surface of the outer body 12.

One of the outer and inner calcification treatment members 16 and 20 includes an expandable treatment member. In the illustrated embodiment, it is the inner calcification treatment member(s) 20 which is (are) the expandable treatment members 20. Alternatively, the outer calcification treatment member could be the expandable treatment member and the inner calcification treatment member could be the fracturing element.

The calcification treatment device 10 may be delivered through a catheter 22 over a guidewire 23 or other suitable device, as is known in the art. In such a case, the inner body 18 may be connected to an inner tube and moved into and out of the inner cavity 14 over the guidewire 23.

Figure 4:
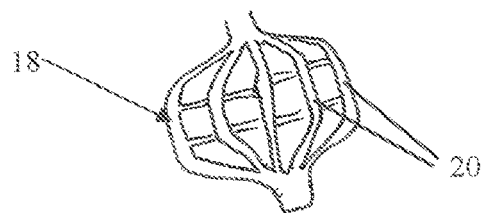
FIG. 4 is a simplified pictorial illustration of expandable treatment members, which may abut against leaflets or other calcified tissue and bear the fracturing force of the fracturing elements, in accordance with a non-limiting embodiment of the present invention.

The expandable treatment member 20 may be generally structured, without limitation, as an expandable stent-like element; One embodiment of the expandable treatment member 20 is shown in FIG. 4, in which the expandable treatment member 20 is arranged for buckling radially outwards. This may be accomplished, without limitation, by designing the structure of expandable treatment member 20 as flexible struts which are axially slidable along a shaft. Sliding the struts against a distal stop causes the struts to bend and the structure to expand outwards. Alternatively, the distal end of the expandable treatment member 20 may be compressed against the proximal end (or vice versa), thereby causing the mid-section to expand outwardly in a generally radial direction.

Figure 5:
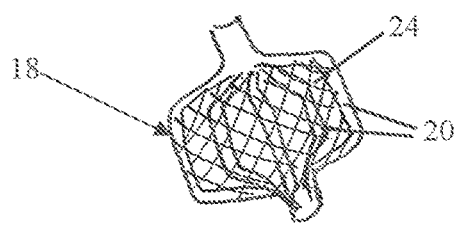
FIG. 5 is a simplified pictorial illustration of expandable treatment members and mesh, which may abut against leaflets or other calcified tissue and bear the fracturing force of the fracturing elements, in accordance with another non-limiting embodiment of the present invention.

Another embodiment of the expandable treatment member 20 is shown in FIG. 5, in which the expandable treatment member 20 includes an expandable mesh or balloon 24. The mesh may be expanded similarly to the way flexible struts are expanded. The balloon may be expanded by injecting a fluid (e.g., air, water or saline) via a lumen in fluid communication with a fluid source (not shown) and the balloon.

The inner body 18 and inner calcification treatment members 20 may be constructed, without limitation, from elastic materials, such as but not limited to, nitinol, cobalt chromium alloys, stainless steel, polymers or any combination thereof.

In accordance with an embodiment of the present invention the expandable treatment member 20 and the one or more fracturing elements 16 are concentric with each other. Alternatively, they are not concentric with each other; they may be concentric during a portion of their operation and non-concentric during other portions of their operation.

Figure 6:
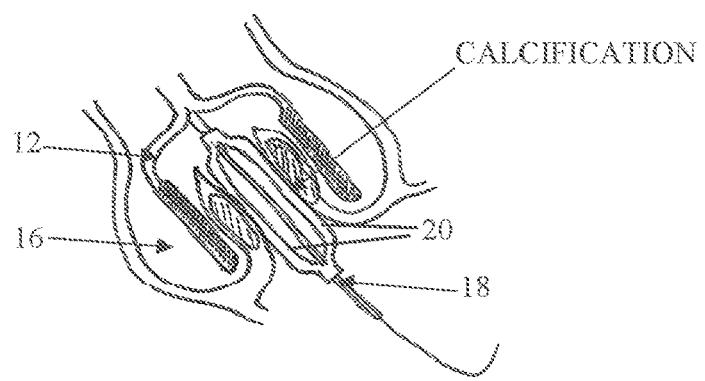
FIG. 6 is a simplified pictorial illustration of the initial position of the calcification treatment device of FIG. 2, showing expandable (ventricular) treatment members and outer (aortic) fracturing elements in a valve (e.g., the aortic valve), wherein the expandable treatment members are in a contracted orientation.
Figure 7:
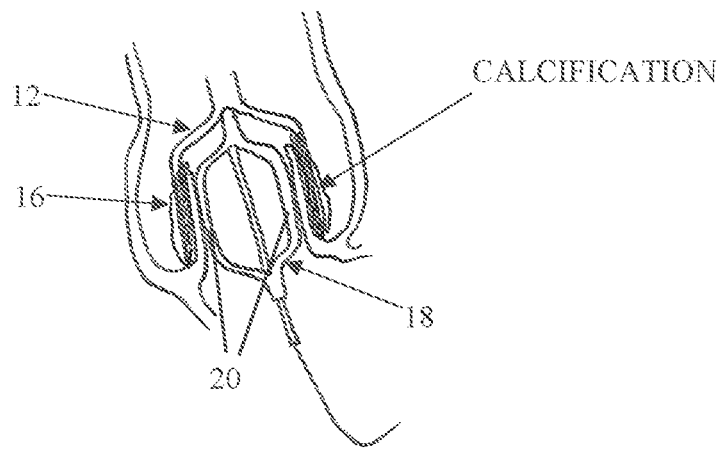
FIG. 7 is a simplified pictorial illustration of the calcification treatment device of FIG. 6, after expansion of the expandable treatment members.

The following is a non-limiting method of using the device of the invention, described with reference to FIGS. 6 and 7. In FIG. 6, the treatment catheter (22 in FIG. 2) has been used to deliver the calcification treatment device to the vicinity of the diseased valve (e.g., aortic valve). The outer body 12 and the outer calcification treatment members 16 are positioned on the arterial side of the aortic leaflets (the body 12 and members 16 form an aortic element). The fracturing elements 16 face radially inwards. The inner body 18 and inner calcification treatment members 20 (which form a ventricular element) are delivered over the guidewire so that part of the ventricular element is located in the ventricle or the ventricular outflow tract, and part extends axially above the cusps of the aortic valve leaflets. Accordingly, in its contracted orientation, the expandable treatment member 20 (with a portion of inner body 18) is passable through cusps of the valve. The two aortic and ventricular elements may be concentrically arranged within the catheter, but this concentricity may be disrupted during operation of the device, such as when the elements are released from the confines of the catheter.

The ventricular element is placed through the aortic valve so that it spans the valve complex. The fracturing elements 16 face radially inwards and are circumferentially arranged around the aortic valve facing the aortic valve leaflets. As seen in FIG. 7, the inner calcification treatment members 20 of the ventricular element are expanded so as to move the aortic valve leaflets outward and open the valve. The leaflets are sandwiched between the ventricular and aortic elements (between inner calcification treatment members 20 and fracturing elements 16). As the inner calcification treatment members 20 of the ventricular element continue to expand and open the calcified valve leaflets outwards, the fracturing elements 16 create breaks or incisions on the aortic side of the aortic valve leaflets. These breaks or incisions weaken and dissect the calcium formation within the valve leaflets and help the leaflets regain lost mobility, so that the leaflets move in a freer manner even when the treatment catheter is removed.

Figure 8:
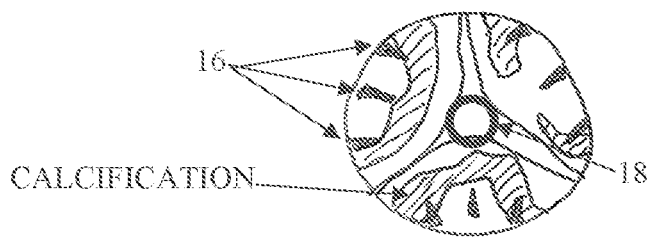
FIG. 8 is a simplified pictorial illustration of locations of the fracturing elements on the valve prior to expansion of the expandable treatment members.

FIG. 8 illustrates locations of fracturing elements 16 on the valve prior to expansion of the expandable treatment members of inner body 18.

Figure 9:
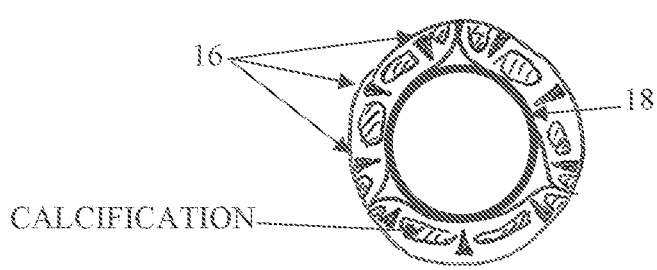
FIG. 9 is a simplified pictorial illustration of locations of the fracturing elements on the valve during expansion of the expandable treatment members.

FIG. 9 illustrates locations of fracturing elements 16 on the valve during expansion of the expandable treatment members of inner body 18.

Figure 10:
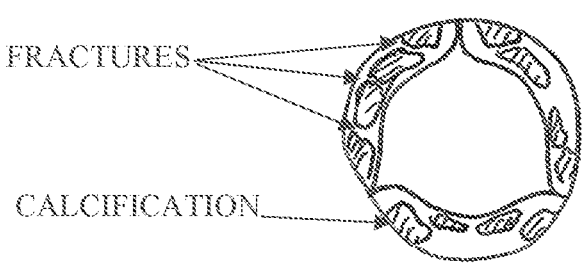
FIG. 10 is a simplified pictorial illustration of the calcified valve after treatment with the calcification treatment device of FIG. 6.

FIG. 10 illustrates the calcified valve after treatment with the calcification treatment device, showing the fractured calcifications.

Figure 11:
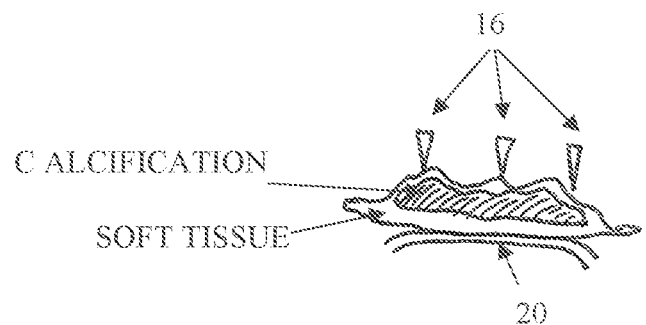
FIG. 11 is a simplified cross-sectional illustration of a calcified leaflet with cutting/fracturing elements on the aortic aspect of the valve and expandable treatment members on the ventricular aspect.

FIG. 11 illustrates a calcified leaflet with fracturing elements 16 on the aortic aspect of the valve and expandable treatment members 20 on the ventricular aspect. It is seen that the fracturing elements 16 may be sharp cutting knife edges, for example.

Figure 12:
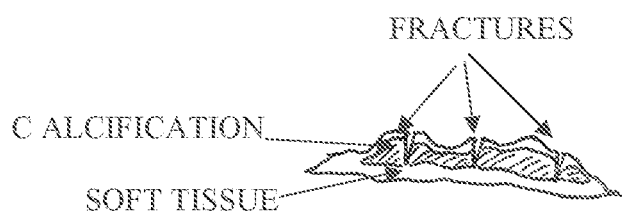
FIG. 12 is a simplified cross-sectional illustration of a calcified leaflet after cutting/fracturing with the treatment device of the invention.

FIG. 12 illustrates a calcified leaflet after fracturing with the treatment device of the invention. The fractures do not extend into the soft tissue.

Figure 13:
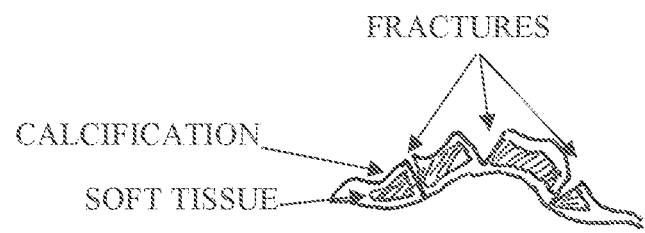
FIG. 13 is a simplified cross-sectional illustration of a calcified leaflet after cutting/fracturing, and showing renewed leaflet mobility.

FIG. 13 illustrates a calcified leaflet after fracturing with the device of the invention, showing renewed leaflet mobility.

Figure 14:
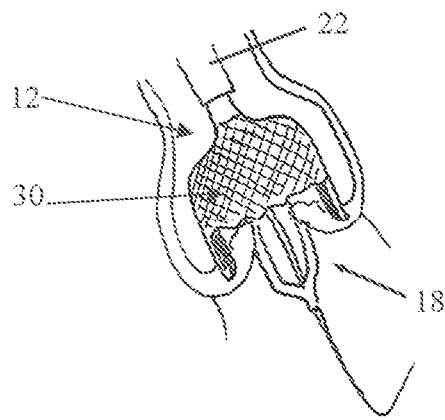
FIG. 14 is a simplified pictorial illustration of an embolic protection filter added to the aortic element (fracturing elements), in accordance with a non-limiting embodiment of the present invention.

Reference is now made to FIG. 14. In some embodiments of the invention, a filter 30 may be attached to the catheter 22 or the outer body 12 so as to form a protective device which may capture any debris caused by the procedure.

Figure 15:
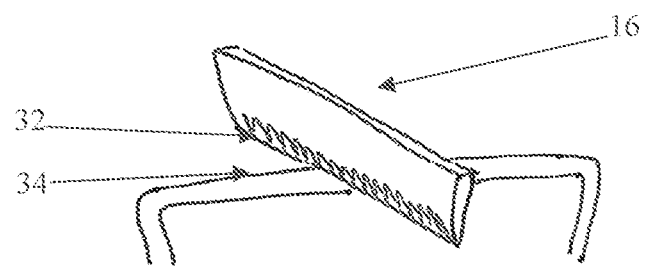
FIG. 15 is a simplified pictorial illustration of intersecting (as opposed to parallel) expansion struts (expandable treatment members), which limit the cutting depth through tissue, in accordance with a non-limiting embodiment of the present invention.

Reference is now made to FIG. 15, which illustrates fracturing element 16 with a knife-edge 32 that fractures against a transverse (i.e., intersecting, as opposed to parallel) expansion strut (expandable treatment member) 34. The intersecting struts may limit the length/extent/width of the fracture.

Figure 16:
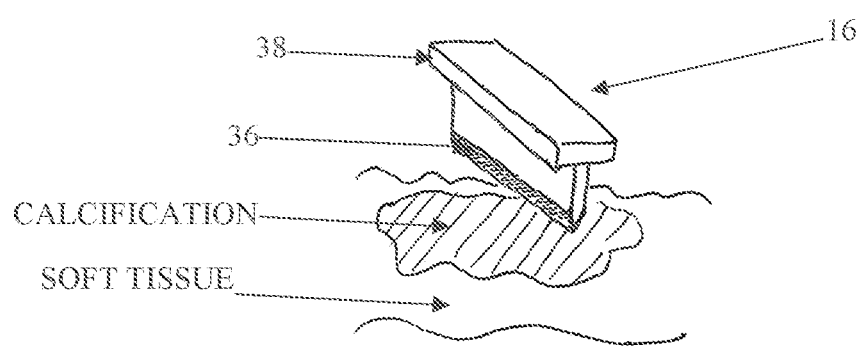
FIG. 16 is a simplified pictorial illustration of a blunt stopper, which limits the cutting depth through soft tissue, in accordance with a non-limiting embodiment of the present invention.

Another example is shown in FIG. 16, which illustrates fracturing element 16 with a knife-edge 36, wherein the fracturing element 16 has structure, such as a (blunt) stopper 38, which limits the cutting depth through soft tissue.

What is claimed is:

1. A calcification treatment device comprising:
an outer body comprising an inner cavity and at least one outer calcification treatment member facing towards said inner cavity;
an inner body movable into said inner cavity and comprising at least one inner calcification treatment member facing towards an inner surface of said outer body, wherein one of said outer and inner calcification treatment members comprises an expandable treatment member and one of said outer and inner calcification treatment members comprises one or more fracturing elements capable of fracturing a calcification of a valve tissue, wherein said one or more fracturing elements comprise blunt structure distanced from a cutting edge of each of said one or more fracturing elements to limit a cutting depth through soft tissue.

2. The calcification treatment device according to claim 1, wherein said expandable treatment member is arranged for buckling radially outwards.

3. The calcification treatment device according to claim 1, wherein said expandable treatment member comprises an expandable mesh.

4. The calcification treatment device according to claim 1, wherein said expandable treatment member comprises an expandable balloon.

5. The calcification treatment device according to claim 1, wherein said at least one inner calcification treatment member comprises the expandable treatment member and said at least one outer calcification treatment member comprises the one or more fracturing elements.

6. The calcification treatment device according to claim 1, wherein said expandable treatment member and said one or more fracturing elements are concentric with each other.

7. The calcification treatment device according to claim 1, wherein said expandable treatment member and said one or more fracturing elements are not concentric with each other.

8. The calcification treatment device according to claim 1, wherein in a contracted orientation said expandable treatment member is passable through cusps of a valve.

9. The calcification treatment device according to claim 1, wherein said blunt structure extends outwards from each of said one or more fracturing elements.

10. The calcification treatment device according to claim 1, wherein said at least one outer calcification treatment member comprise discrete members separated from each other by gaps.

11. The calcification treatment device according to claim 1, wherein said at least one outer calcification treatment member comprise one continuous member that spans part of or all of a periphery of said outer body.

12. The calcification treatment device according to claim 1, wherein said at least one outer calcification treatment member comprises individual fracturing elements spaced from one another.

13. The calcification treatment device according to claim 12, wherein said at least one outer calcification treatment member comprises individual fracturing elements spaced from one another with a varying spacing.

* * * * *